United States Patent [19]
Otterbeck et al.

[11] Patent Number: 5,914,122
[45] Date of Patent: Jun. 22, 1999

[54] STABLE BUDESONIDE SOLUTIONS, METHOD OF PREPARING THEM AND USE OF THESE SOLUTIONS AS ENEMA PREPARATIONS AND PHARMACEUTICAL FOAMS

[75] Inventors: Norbert Otterbeck, Uberlingen; Reimund Kuhn, Freiamt, both of Germany

[73] Assignee: Dr. Falk Pharma GmbH, Freiburg, Germany

[21] Appl. No.: 08/860,136

[22] Filed: Jun. 27, 1997

[30] Foreign Application Priority Data

Dec. 27, 1994 [DE] Germany ............................. 44 46 891

[51] Int. Cl.$^6$ ...................................... A61F 2/02
[52] U.S. Cl. ............................. 424/434; 424/423
[58] Field of Search ..................... 424/423, 434

[56] References Cited

U.S. PATENT DOCUMENTS

| | | |
|---|---|---|
| 4,383,992 | 5/1983 | Lipari . |
| 5,725,872 | 3/1998 | Stamm et al. .......................... 424/436 |

FOREIGN PATENT DOCUMENTS

| | | |
|---|---|---|
| 468 555 | 4/1992 | European Pat. Off. . |
| 9314973 | 12/1993 | France . |
| 94 16710 | 7/1994 | WIPO . |
| 95 14474 | 6/1995 | WIPO . |

OTHER PUBLICATIONS

Atemwegs–Und Lungenkrankheiten (20)7, 381–382 (1994), J. Derbacher et al, "Physikalische Eigenschaften . . . ".

J. Pharm. Sci., 84(6), 677–681 (1995) H. Nolen et al, "Budesonide–Beta–D–Glucuronide . . . ".

*Primary Examiner*—Carlos Azpuru
*Attorney, Agent, or Firm*—Michael N. Meller

[57] ABSTRACT

A stable budesonide solution with a pH not exceeding 6.0 in which the budesonide is dissolved in a solvent which may be water, an alcohol such as ethanol, isopropanol or propylene glycol, or a water/alcohol mixture. The solution preferably also contains a stabilizer such as sodium ethylenediaminetetraacetic acid, cyclodextrins or mixtures thereof. The stable budesonide solution is useful as the active ingredient in a rectal enema or a rectal foam.

22 Claims, No Drawings

STABLE BUDESONIDE SOLUTIONS, METHOD OF PREPARING THEM AND USE OF THESE SOLUTIONS AS ENEMA PREPARATIONS AND PHARMACEUTICAL FOAMS

BACKGROUND OF THE INVENTION

1. Field of the Invention

The present invention relates to stable budesonide solutions, the process for their preparation, and their use for producing pharmaceutical preparations, in particular enemas and pharmaceutical foams.

2. Background Art

Budesonids (INN; 16α,17-butylidenedioxy-11β,21-dihydroxy-1,4-pregnadiene-3,20-dione) is a known active substance of the corticoid series which is employed in particular for the treatment of bronchial disorders, but also in cases of inflammatory bowel disorders such as Crohn's disease and, in particular, ulcerative colitis. It has proven particularly suitable for the last-mentioned indication to administer rectal drug forms such as enema preparations or pharmaceutical foams in compressed gas packs, because the active substance is employed directly at the site of the disorder, and budesonide is especially topically effective.

Budesonide is a racemate consisting of a mixture of the two diastereomers 22R and 22S. The racemate can be employed for the purposes of the present invention, but the 22R diastereomer is preferably employed because this is more active in pharmacological respects by a factor of about 2–3. Processes for fractionating the enantiomers are known, for example from EPA 92.901023.9.

Because of its lipophilicity, budesonide is virtually insoluble in water but is readily soluble in alcohols. An adequate amount of active substance can be dissolved by the use of solubilizers such as organic, water-soluble alcohols. However, the solutions obtained in this way prove to have too little stability for pharmaceutical use because large amounts of the active substance are decomposed within a short time.

Because of this instability, budesonide preparations which can be used directly by the patient in the administration form ready for use are unknown. Although budesonide-containing enemas are currently marketed in some countries, in these cases the enemas are not ready for use but comprise a type of combination of tablets containing active substance and enema bottles filled with water. Before administration, the patient must in each case remove a tablet, introduce it into the opened enema bottle, wait until the tablet has disintegrated and shake the bottles vigorously before use in order to disperse the active substance as homogeneously an possible in the form of a suspension.

This laborious and troublesome preparation of the enema ready for use can be only inadequately accomplished in particular by frail patients. Homogeneous dispersion of the active substance can be achieved only inadequately by this process, and complete administration of the active substance by squeezing of the enema bottle can scarcely be guaranteed because there is a tendency for the suspended active substance to settle out on the bottom of the bottle in a short time after preparation of the final form.

Although rectal administration of budesonide by means of rectal foams has advantages in respect of convenience of use, the problem here is to provide budesonide solutions which have adequate stability for administration in compressed gas packs. Budesonide-containing rectal foams have therefore not hitherto been disclosed.

OBJECT OF INVENTION

One object of the present invention is to provide adequately stable solutions of budesonide.

This object is achieved by budesonide solutions which have a pH of 6 or below.

SUMMARY OF THE INVENTION

The invention relates to stable budesonide solutions with a pH of 6.0 or below. The Budesonide is dissolved according to the invention in water, alcohol or a water/alcohol mixture.

DETAILED DESCRIPTION OF THE INVENTION

It has been found, completely surprisingly, that the stability of budesonide-containing solutions depends crucially on the pH. The stability of the solutions increases as the pH decreases. The budesonide solutions according to the invention can be prepared on an aqueous and/or alcoholic basis, it also being possible to dissolve budesonide in an aqueous, alcoholic mixture.

It has been found, completely surprisingly, in the framework of the present invention that the pH has a crucial influence on the stability of the budesonide solution, specifically in aqueous, aqueous-alcoholic or alcoholic solution.

Table 1 which is shown hereinafter proves the stability of an aqueous solution of budesonide and Table 2 shows the stability of an alcoholic solution (propylene glycol) of budesonide as a function of the storage time and the pH.

TABLE 1

Stability of budesonide solutions according to the invention (2 mg/60 ml of $H_2O$) as a function of the storage time

| | Contents[1] after storage for 14 days at | |
|---|---|---|
| pH | 20° C. | 40° C. |
| 7.0 | 96.5% | 71.2% |
| 6.5 | 96.4% | 77.1% |
| 6.0 | 97.6% | 84.8% |
| 5.5 | 97.4% | 87.6% |
| 5.0 | 97.6% | 90.0% |
| 4.5 | 97.3% | 93.0% |
| 4.0 | 98.7% | 95.2% |
| 3.5 | 99.8% | 96.6% |
| 3.0 | 100.0% | 97.9% |

[1] Initial value after t = 0 days equal to 100%

It is evident from Table 1 above that the stability of the solutions increases as the pH decreases. Even after storage at 20° C. and pH 3.0 for 14 days, the active substance is still 100% present. Even on storage at a distinctly higher temperature, that is to say at 40° C. and pH 3.0, there is still 97.9% budesonide in the solution after 14 days.

TABLE 2

Stability of budesonide solutions according to the invention (2 mg/4 g in propylene glycol) as a function of the storage time

| | Content after storage at | | |
|---|---|---|---|
| pH | 0 months | 3 months 25° C. | 3 months 40° C. | 6 months 40° C. |
| 7.5 | 100.0% | 80.6% | 44.4% | 15.3% |
| 5.0 | 100.0% | 103.0% | 96.5% | 89.5% |
| 2.8 | 100.0% | 99.4% | 98.7% | 95.2% |

It is evident from Table 2 above that the stability of the solutions increases as the pH decreases.

The losses of active substance at pH values of 4.0 and below are sufficiently low to be of an acceptable magnitude as a function of the storage time for pharmaceutical products.

For pharmaceutical use, the preferred pH values of the form ready for use are ≧3.5 for use as enema or else as rectal foam because of the physiological factors and taking account of the amount of about 30 to 100 ml to be administered for enemas and of about 4 g in the case of rectal foams.

Any pharmaceutically acceptable organic and inorganic acids can be used to adjust the pH, for example hydrochloric acid, phosphoric acid, citric acid or tartaric acid.

In order to increase the stability further, for example to save transport and storage costs, or else for use as non-rectal administration form, it is also possible to prepare concentrated budesonide solutions with a pH ≦3.5. If it is necessary for subsequent use to adjust the pH to a physiologically tolerated value >3.5, this can take place only shortly before use. This can happen, for example, by dilution or by addition of a base. The dilution process then increases the pH.

In other preferred embodiments, the budesonide solutions according to the invention have an addition of sodium EDTA (sodium ethylenediaminetetraacetic acid; Komplexon), which further increases the stability.

In another preferred embodiment of the present invention, the stability of the solution can be increased by using cyclodextrins, preferably hydroxy-propyl-β-cyclodextrin or γ-cyclodextrin. Addition of cyclodextrins also makes it possible to use more concentrated solutions of budesonide.

The invention therefore relates to stable budesonide solutions with a pH of 6.0 or below. The budesonide is dissolved according to the invention in water, alcohol or a water/alcohol mixture.

The alcohols used for the purposes of the present invention are preferably propylene glycol, ethanol or isopropanol.

When an alcohol/water mixture is employed, the ratio of alcohol to water is between 100:0 and 80:20, preferably between 98:2 and 93:7.

The budesonide content in the solution ready for use is between 0.001 and 1% by weight, preferably between 0.01 and 0.1% by weight and, in the case of enemas, is particularly preferably 0.001 to 0.1% by weight.

The solutions according to the invention may furthermore contain ancillary substances customarily used in corresponding pharmaceutical formulations. These ancillary substances may be suitable for solubilizing corticoids. The skilled worker is familiar with ancillary substances of this type.

Conventional ancillary substances are those which influence, normally increase, the viscosity of the solution, preservatives such as ethanol, chlorobutanol, benzyl alcohol, phenylethanol, sorbic acid, benzoic acid, sodium disulfite, p-hydroxybenzoates, phenol, m-cresol, p-chloro-m-cresol, quats, chlorohexidine, thickeners such as gelatin, tragacanth, pectin, cellulose derivatives (for example methylcellulose, hydroxypropylmethylcellulose, carboxymethylcellulose sodium), polyvinylpyrrolidone, polyvinyl alcohol, polyacrylic acids, xanthan gum, acids such as acetic acid, citric acid, tartaric acid, hydrochloric acid, phosphoric acid; bases such as potassium hydroxide, sodium hydroxide; buffer substances such as hydrochloric acid buffer, phthalate buffer, phosphate buffer, borate buffer, acetate buffer or citrate buffer. In order to increase the solubility of the active substance, it is suitable, for example, to add sufficient amounts of alcohols such as ethanol, isopropanol, glycerol, propylene glycol, polyethylene glycols or to use solubilizers such as, for example, cyclodextrins, preferably β-cyclodextrin, hydroxypropyl-β-cyclodextrin and/or γ-cyclodextrin.

If the budesonide solutions according to the invention are intended for use as rectal foams, it is necessary to add those customary ancillary substances which first make it possible for the dispersion to form. Ancillary substances of this type are emulsifiers known to the skilled worker, such as Eumulgins and various Lanette types. It is furthermore possible to add preservatives such as sorbic acid, parahydroxybenzoates, benzoic acid, acids such as acetic acid, citric acid, tartaric acid, hydrochloric acid and phosphoric acid.

In the case of rectal foams, suitable propellant gases are also introduced into the pressure packs. Even if chlorofluorocarbon gases were suitable as propellant gases, the use of these gases tends to be avoided at present for reasons of environmental protection. The propellant gases preferably used are therefore hydrocarbons such as isobutane, n-butane or propane/n-butane mixtures.

The pH of the budesonide solutions according to the invention is 6.0 or below. A range between 5.0 and 3.5 is preferred, and the pH range between 4.5 and 4.0 is particularly preferred.

Budesonide is present in the solutions according to the invention in an amount between 0.001 and 1% by weight, with the concentration in solutions intended to be used as enemas being lower than in solutions intended for rectal foams. The preferred concentration in solutions for enemas is between 0.01 and 0.1% by weight, and the preferred range for rectal foams is between 0.01 and 0.1% by weight.

Sodium EDTA is preferably added in an amount of 0.01 to 1.0% by weight, with a range from 0.01 to 0.1% by weight being preferred for enemas and a concentration of 0.05 to 1% by weight being preferred for rectal foams.

Whereas cyclodextrins are added as solubilizers, this preferably takes place in an amount between 0.05 and 0.5% by weight, with addition of about 0.1% by weight being preferred.

Solutions for enemas are prepared by processes known per se. It is possible, for example, to incorporate an ethanolic stock solution of budesonide into an aqueous solution of the other ingredients with homogenization. The use of an antioxidant or exclusion of oxygen, and measures in the area of protection from light are not specifically necessary but they may improve the quality and the stability of the resulting products. For rectal use, the finished solution is then dispensed into a conventional flexible enema bottle with applicator tip, both of which are preferably produced from opaque plastic.

The preparation of solutions for rectal foams is also known in the prior art. For example, the preservative and the emulsifiers required for foam formation can be dissolved in the appropriate solution, preferably the suitable alcohol. The active substance is then incorporated as alcoholic stock solution into this solution. In the last step, Komplexon and the appropriate acid, dissolved in a small amount of water, are stirred into the alcoholic solution with homogenization.

If the budesonide solution according to the invention is used to produce a rectal foam, the finished solution is introduced into suitable compressed gas packs which are provided with commercially obtainable valve systems as single or multiple dose devices, and a propellant gas is added. The packs additionally contain an applicator tip made of plastic. Because of the chemical and physical properties of the stable budesonide solution according to the invention, the foam is inevitably generated in the rectum on administration.

In a preferred embodiment, the stable budesonide solutions according to the invention are used to produce enemas or rectal foams. Other use forms such as, for example, use as metered aerosol, inhalation spray or else as drops, syrup or elixirs are likewise possible and can easily be produced by the skilled worker on the basis of the present description. The invention is explained in detail by means of the following examples.

EXAMPLE 1

A solution is prepared by the process described above and is dispensed into appropriate plastic bottles and contains the following ingredients per 60 g enema bottle:

| | |
|---|---|
| budesonide | 2 mg |
| β-cyclodextrin, hydroxypropyl-β-cyclodextrin (0.9) or γ-cyclodextrin | 60 mg |
| sodium EDTA | 30 mg |
| sodium benzoate | 300 mg |
| xanthan gum | 360 mg |
| 2N HCl ad pH 4.0 | |
| ethanol | 400 mg |
| water ad | 60.00 mg |

The solution produced in this way proved to be stable even after storage at 40° C. for several weeks.

EXAMPLE 2

Enema produced by the customary process, containing

| | |
|---|---|
| budesonide | 2 mg |
| sodium benzoate | 300 mg |
| sodium EDTA | 30 mg |
| propylene glycol | 500 mg |
| xanthan gum | 360 mg |
| 2N hydrochloric acid ad pH 3.5 | 60.00 mg |

The enema produced in this way proved to be stable after storage at 40° C. for several weeks.

EXAMPLE 3

An aqueous solution is produced as in Example 1 and contains the following ingredients:

| | |
|---|---|
| budesonide | 2 mg |
| β-cyclodextrin, hydroxypropyl-β-cyclodextrin (0.9) or γ-cyclodextrin | 60 mg |
| sodium benzoate | 300 mg |
| xanthan gum | 360 mg |
| 2N HCl ad pH 4.0 | |
| ethanol | 400 mg |
| water ad | 60.00 mg |

The solution produced in this way proved to be stable even after storage at room temperature for several weeks.

EXAMPLE 4

An aqueous solution is produced as in Example 1 and contains the following ingredients:

| | |
|---|---|
| budesonide | 2 mg |
| sodium EDTA | 30 mg |
| sodium benzoate | 300 mg |
| xanthan gum | 360 mg |
| 2N HCl ad pH 4.0 | |
| ethanol | 400 mg |
| water ad | 60.00 mg |

The solution produced in this way proved to be stable even after storage at room temperature for several weeks.

EXAMPLE 5

An aqueous solution is produced as in Example 1 and contains the following ingredients:

| | |
|---|---|
| budesonide | 2 mg |
| sodium benzoate | 300 mg |
| xanthan gum | 360 mg |
| 2N HCl ad pH 4.0 | |
| ethanol | 400 mg |
| water ad | 60.00 mg |

The solution produced in this way proved to be stable even after storage at room temperature for several weeks.

EXAMPLE 6

Investigation of the stability of the solutions according to the invention

The formulations in the following Table 3 were produced as in Example 1 and investigated for their stability after storage for 1 to 39 weeks. The following results were obtained.

TABLE 3

| | Content[1] Stress time in . . . weeks at 40° C. | | | | | |
|---|---|---|---|---|---|---|
| | 1 | 4 | 6 | 11 | 16 | 39 |
| pH 5, without additions | 96.1% | 67.6% | 60.2% | 56.6% | | |
| pH 4, with EDTA, with γ-cyclodextrin | | | 100.0% | 99.6% | 99.8% | 97.3% |
| pH 4, with EDTA, with hydroxypropyl-β-cyclodextrin (molar degree of substitution 0.9) | | | 100.0% | 94.7% | 95.0% | 89.4% |
| pH 4, with EDTA, with propylene glycol | | | | 98.8% | 93.1% | |

[1]Initial value at t = 0 weeks = 100%

The above test results prove that the aqueous budesonide solutions according to the invention with a pH below 6 are still stable even after storage for several weeks. Solutions which contain EDTA and a cyclodextrin are particularly stable. Thus, these solutions still contain 100% of active substance even after storage at 40° C. and pH 4 for six weeks.

EXAMPLE 7

A solution is prepared by the process described above and is dispensed into appropriate compressed gas packs (for example aluminum monoblock can, 55 ml, with liquid valve, shield and metering head) with the addition of a propellant gas (pressure >1.5 bar, such as, for example, isobutane, n-butane, propane/n-butane mixtures).

The solution contains the following ingredients

| | |
|---|---|
| budesonide | 0.01820 g |
| Lanette 0 | 0.45500 g |
| Eumulgin B1 | 0.09100 g |
| Eumulgin B2 | 0.09100 g |
| sorbic acid | 0.00845 g |
| Komplexon | 0.03000 g |
| citric acid ad pH 3.5 | 0.01000 g |
| aqua purificata | 0.90000 g |
| propylene glycol ad | 35.0000 g |

The solution produced in this way proved to be stable after storage at 40° C. for several months.

EXAMPLE 8

| | |
|---|---|
| budesonide | 0.01820 g |
| Lanette 0 | 0.45500 g |
| Eumulgin B1 | 0.09100 g |
| Eumulgin B2 | 0.09100 g |
| benzoic acid | 0.06000 g |
| citric acid ad pH 4.0 | q.s. |
| aqua purificata | 0.90000 g |
| propylene glycol ad | 35.0000 g |

The solution produced in this way proved to be stable after storage at 40° C. for several months.

EXAMPLE 9

| | |
|---|---|
| budesonide | 0.01820 g |
| Lanette 0 | 0.45500 g |
| Eumulgin B1 | 0.09100 g |
| Eumulgin B2 | 0.09100 g |
| Komplexon | 0.03000 g |
| tartaric acid ad pH 4.5 | q.s. |
| aqua purificata | 0.90000 g |
| propylene glycol ad | 35.0000 g |

The solution produced in this way proved to be stable after storage at 40° C. for several months.

EXAMPLE 10

Investigations of the stability of the solutions according to the invention

Formulations were produced as in Example 7 with different pH values and were investigated for their stability after storage for 0–6 months. The following results were obtained:

TABLE 4

| | Content after storage at | | | |
|---|---|---|---|---|
| pH | 0 months | 3 months 25° C. | 3 months 40° C. | 6 months 40° C. |
| 7.5 without additions | 100.0% | 90.4% | 75.0% | not determined |
| 7.5 with Komplexon | 100.0% | 103.0% | 96.5% | 89.5% |
| 4.5 (94073) with Komlexon, with citric acid | 100.0% | 102.5% | 97.8% | 94.6% (9 months) |
| 4.0 (95030) with Komlexon, with citric acid | 100.0% | 97.6% | 98.0% | — |
| 3.5 (95035) with Komlexon, with citric acid | 100.0% | 100.8% | 100.2% | — |

The above test results prove that the alcoholic budesonide solutions according to the invention with a pH below 6 are still stable even after storage for several months. Solutions which additionally contain Komplexon are particularly stable. The losses of active substance occurring even after storage at 40° C. for 6–9 months are extremely small.

We claim:

1. A stable budesonide solution with a pH not exceeding 6.0 in which the budesonide is dissolved in a solvent selected from the group consisting of water, alcohol and a water/alcohol mixture and wherein the alcohol is selected from the group consisting of ethanol, isopropanol and propylene glycol.

2. A stable budesonide solution as in claim 1, which comprises a stabilizing additive selected from the group consisting of sodium ethylenediaminetetraacetic acid, cyclodextrins and mixtures thereof.

3. A stable budesonide solution with a pH not exceeding 6.0 in which the budesonide is dissolved in a solvent selected from the group consisting of water, alcohol and a water/alcohol mixture and wherein the alcohol is selected from the group consisting of ethanol, isopropanol and propylene glycol, which comprises 0.001 to 0.1% by weight of budesonide.

4. A stable budesonide solution with a pH not exceeding 6.0 in which the budesonide is dissolved in a solvent selected from the group consisting of water, alcohol and a water/alcohol mixture and wherein the alcohol is selected from the group consisting of ethanol, isopropanol and propylene glycol, further comprising 0.05 to 1.0% by weight of cyclodextrins.

5. A stable budesonide solution as in claim 1, with a pH not exceeding 6.0 comprising 0.001 to 0.1% by weight of budesonide and stabilizing additives selected from the group consisting of 0.001 to 0.1% by weight of sodium ethylenediaminetetraacetic acid; 0.05 to 1.0% by weight of cyclodextrins and a mixture of said amounts of sodium ethylenediaminetetraacetic acid and cyclodextrins.

6. A process for producing a stable budesonide-containing solution with a pH not exceeding 6.0 which comprises dissolving the budesonide in a solvent selected from the group consisting of water, alcohol and a water/alcohol mixture, with the alcohol selected from the group consisting of ethanol, isopropanol and propylene glycol, and adjusting the pH of the budesonide solution to a value not exceeding 6.0.

7. A process as in claim 6, which comprises adding thereto a stabilizing additive selected from the group consisting of sodium ethylenediaminetetraacetic, cyclodextrins and a mixture thereof.

8. A process as in claim 6, wherein the solution comprises 0.001 to 1% by weight of budesonide and the stabilizing additive is selected from the group consisting of 0.001 to 1% by weight of sodium ethylenediaminetetraacetic acid, 0.05 to 1.0% by weight of cyclodextrins and a mixture of said amounts of sodium ethylenediaminetetraaceticacetic acid and cyclodextrins.

9. An enema solution which comprises as the active ingredient, a stable budesonide solution as in claim 1.

10. An enema solution which comprises as the active ingredient, a stable budesonide solution as in claim 2.

11. An enema solution which comprises as the active ingredient, a stable budesonide solution as in claim 3.

12. An enema solution which comprises as the active ingredient, a stable budesonide solution as in claim 4.

13. An enema solution which comprises as the active ingredient, a stable budesonide solution as in claim 5.

14. An enema solution which comprises as the active ingredient, stable budesonide solution as in claim 6.

15. A rectal foam which comprises, as the active ingredient, a stable aqueous budesonide solution as in claim 1.

16. A rectal foam which comprises as the active ingredient, a stable budesonide solution as in claim 2.

17. A rectal foam which comprises as the active ingredient, a stable budesonide solution as in claim 3.

18. A rectal foam which comprises as the active ingredient, a stable budesonide solution as in claim 4.

19. A rectal foam which comprises as the active ingredient, a stable budesonide solution as in claim 5.

20. A rectal foam which comprises as the active ingredient, a stable budesonide solution as in claim 6.

21. A stable budesonide solution with a pH not exceeding 6.0 in which the budesonide is dissolved in a solvent selected from the group consisting of water, alcohol and a water/alcohol mixture and wherein the alcohol is selected from the group consisting of ethanol, isopropanol and propylene glycol, further comprising 0.001 to 0.1% by weight of sodium ethylenediaminetetraacetic acid.

22. A stable budesonide solution with a pH not exceeding 6.0 in which the budesonide is dissolved in a solvent selected from the group consisting of water, alcohol and a water/alcohol mixture and wherein the alcohol is selected from the group consisting of ethanol, isopropanol and propylene glycol, comprising 0.001 to 0.1% by weight of budesonide and stabilizing additives selected from the group consisting of 0.001 to 0.1% by weight of sodium ethylenediaminetetraacetic acid, 0.05 to 1.0% by weight of cyclodextrins and a mixture of said amounts of sodium ethylenediaminetetraacetic acid and cyclodextrins.

* * * * *